United States Patent
Spindelbalker

(10) Patent No.: US 6,324,702 B1
(45) Date of Patent: Dec. 4, 2001

(54) LOOKING GLASS FOR SKI GOGGLES

(75) Inventor: Rupert Spindelbalker, Puchenau (AT)

(73) Assignee: Silhouette International Schmied GmbH & Co. KG, Linz (AT)

( * ) Notice: Subject to any disclaimer, the term of this patent is extended or adjusted under 35 U.S.C. 154(b) by 0 days.

(21) Appl. No.: 09/623,349

(22) PCT Filed: Feb. 12, 1999

(86) PCT No.: PCT/AT99/00036

§ 371 Date: Sep. 1, 2000

§ 102(e) Date: Sep. 1, 2000

(87) PCT Pub. No.: WO99/44555

PCT Pub. Date: Sep. 10, 1999

(30) Foreign Application Priority Data

Mar. 5, 1998 (AT) ........................................................ 379/98

(51) Int. Cl.⁷ .................................................................. A61F 9/02
(52) U.S. Cl. .................................................................. 2/435
(58) Field of Search .............................. 2/426, 427, 430, 2/432, 435, 436, 445

(56) References Cited

U.S. PATENT DOCUMENTS

| | | |
|---|---|---|
| 1,562,350 | 11/1925 | Luckey . |
| 3,705,760 | 12/1972 | Langendorfer et al. . |
| 5,018,223 | 5/1991 | Dawson et al. . |
| 5,555,038 | 9/1996 | Conway . |
| 5,642,530 | * 7/1997 | Parks ......................................... 2/435 |
| 5,668,618 | * 9/1997 | Simioni ................................. 351/44 |

FOREIGN PATENT DOCUMENTS

| | | |
|---|---|---|
| 1 091 871 | 10/1960 | (DE) . |
| 2 317 088 | 10/1974 | (DE) . |
| 0 446 698 | 5/1997 | (EP) . |
| 524196 | 8/1939 | (GB) . |
| 2284679 | 6/1995 | (GB) . |
| WO92/07630 | 5/1992 | (WO) . |

* cited by examiner

*Primary Examiner*—John J. Calvert
*Assistant Examiner*—Katherine Moran
(74) *Attorney, Agent, or Firm*—Collard & Roe, P.C.

(57) ABSTRACT

The description relates to a double lens (1) for skiing goggles with a curved outer lens (2) and an equally curved inner lens (3) made of a cellulose propionate foil, arranged at a distance from the outer lens (2), which is connected with the outer lens (2) via a sealing tape (4) at the edge. To ensure a favorable fogging behaviour it is suggested that both the outer lens (2), made of injection-molded polycarbonate, and the inner lens (3), made of a vacuum-formed cellulose propionate foil, are curved spherically and that the outer lens (2) is provided with a hygroscopic coating (7) at its inner side.

1 Claim, 1 Drawing Sheet

LOOKING GLASS FOR SKI GOGGLES

FIELD OF THE INVENTION

The invention relates to a double lens for skiing goggles with a curved outer lens and an equally curved inner lens, made of a cellulose propionate foil, that is arranged at a distance from the outer lens and connected with the outer lens via a sealing strip on the edge.

DESCRIPTION OF THE PRIOR ART

To avoid fogging of the lens of skiing goggles with condensed steam as far as possible, it is known to apply double lenses interconnected at a distance to each other via a sealing strip on the edge. The heat insulation due to the air space between the outer and the inner lens provides for an appropriate temperature difference between the two lenses, whereby, because of the related shifting of the dew point, the tendency of fogging of the lens is clearly reduced compared with a single lens, particularly when both lenses are made of a material with a surface quality impeding fogging with condensed steam, as this is the case with cellulose priopionate foils. However, the disadvantage of the double lenses made of cellulose propionate foils is that these foils have a comparably low mechanical strength and can therefore not be considered scratch-resistant. Furthermore, in spite of the double lens design of the lens and the favorable fogging behaviour, there may still be fogging of the lens with condensed steam under unfavorable conditions of temperature and humidity, which impedes the vision through the skiing goggles.

SUMMARY OF THE INVENTION

The invention has therefore the objective to design a double lens for skiing goggles of the above mentioned kind in such a way that not only the mechanical strength of the lens is increased, but that the fogging behaviour is improved, too.

The objective is achieved by the feature that both the outer lens, made of injection-molded polycorbonate, and the inner lens, made of vacuum-formed cellulose propionate foil, are curved spherically and that the outer lens is provided with a hygroscopic layer on its inside.

Compared with conventional skiing goggles, which are provided with a cylindrical curvature to adapt the skiing goggles to the head shape, the air volume enclosed by the skiing goggles between the head of the wearer and the lens is increased because of the spherical curvature of both the outer and the inner lens, which has a favorable effect on the fogging behaviour of the skiing goggles, and in fact to a surprising extent. As the outer lens is manufactured of polycarbonate in an injection molding process, the desired curvature is achieved relatively easily via an appropriate design of the mold. However, as far as the spherical curvature of the inner lens is concerned, there are difficulties, as it is made up of a cellulose propionate foil that, for optical reasons, cannot easily be reshaped. Only by way of vacuum-forming of the applied cellulose propionate foil the desired spherical curvature of the inner lens can be ensured without adversely affecting the optical quality of the lens, provided that molecule drawing during deep-drawing is kept accordingly low.

To be able to combine a high resistance to breakage with a good scratch resistance, it is known to manufacture lenses of polycarbonate. However, with the application of polycarbonate lenses, the particularly good fogging behaviour of cellulose propionate foils is given up. As an embodiment of the lens according to the invention combines an outer lens of polycarbonate with an inner lens of a cellulose propionate foil, and as the inside of the outer lens is additionally provided with a hygroscopic coating, this disadvantage otherwise occurring with lenses of polycarbonate is of no consequence, so that, by combining the specified measures together with the spherical curvature of the lens, a low tendency to fogging of such a lens is achieved, even under unfavorable conditions of temperature and humidity.

BRIEF DESCRIPTION OF THE DRAWING

The drawing depicts an example of the subject matter of the invention.

DESCRIPTION OF THE PREFERRED EMBODIMENTS

Figure 1:
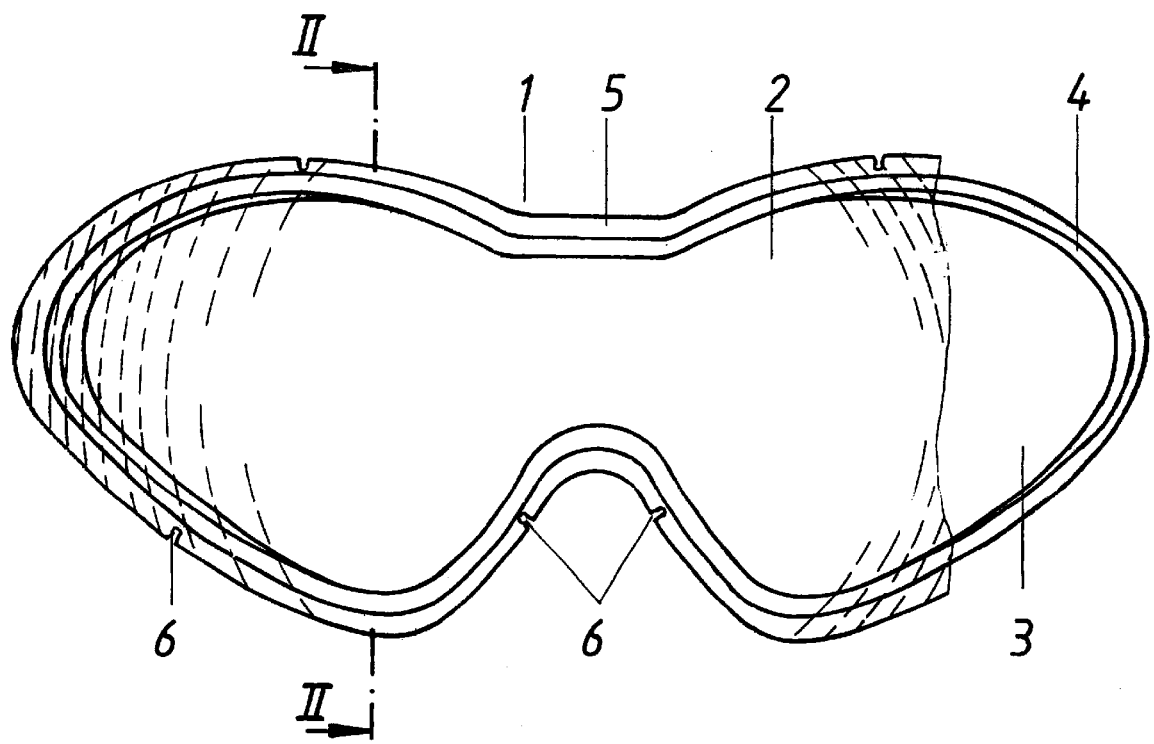
FIG. 1 shows a lens for skiing goggles according to the invention in a partly upright and schematic projection and FIG. 2 depicts a section following the line II—II of FIG. 1.
Figure 2:
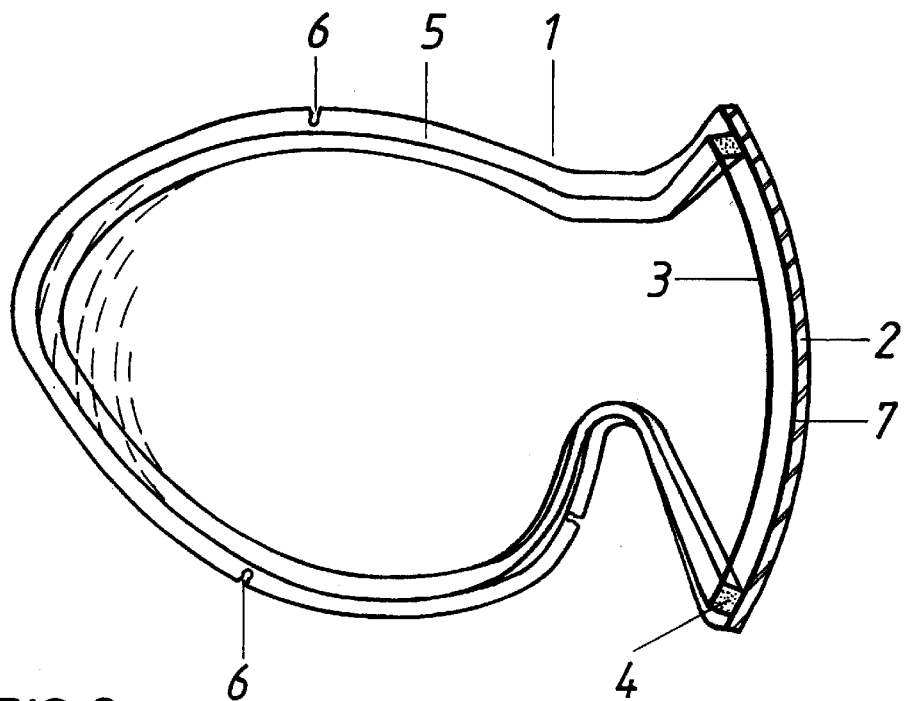

The depicted lens 1 consists of an outer lens 2 made of polycarbonate and an inner lens 3 made of a cellulose propionate foil, connected with the outer lens 2 via a sealing strip 4 at the edge, closed along the circumference. This sealing strip 4 is made of closed-pore cellular material and glued with the two lenses 2 and 3. The outer lens 2 projects over the sealing strip 4 with a rim 5 and is provided with recesses 6 in the area of the rim 5, by means of which the lens 1 is conventionally fastened in a frame-like carrier of the skiing goggles.

As opposed to conventional double lenses, the lens 1 according to the invention is not curved cylindrically but spherically to adapt to the shape of the head, so that both the outer lens 2 and the inner lens 3 are at least roughly spherical. Because of this spherical curvature of the lens 1 the air volume enclosed by the skiing goggles between the lens 1 and the wearer of the goggles is increased, whereby the fogging behaviour of the skiing goggles, in combination with the other measures, is improved to a suprisingly high extent. These additional measures with respect to an improved fogging behaviour consist in the fact that the more unfavourable fogging behaviour of the outer lens 2 made of polycarbonate, compared with that of the inner lens made of cellulose propionate, is compensated by a hygroscopic coating 7 on the inside of the outer lens 2. In this context it must be considered that the air space between the two lenses 2 and 3 cannot be sealed off dampproof, as the plastics used do not form a complete vapour barrier.

While the outer lens 2 made of polycarbonate can be manufactured by way of a conventional injection molding process, the inner lens 3 is made of a cellulose propionate foil, which raises a problem with respect to the spherical curvature, if the optical quality shall not be adversely affected. Therefore, the spherical curvature of the inner lens 3 is achieved by way of a vacuum-forming process, with optical distortions being avoided by ensuring a low molecule drawing.

What is claimed is:

1. Double tens (1) for skiing goggles with a curved outer lens (2) and an equally curved inner lens (3) made of cellulose propionate foil arranged at a distance from the outer lens (2), which is connected with the outer lens (2) via a sealing tape (4) at the edge, characterized in that both the outer lens (2), made of injection-molded polycarbonate, and the inner lens (3), made of a vacuum-formed cellulose propionate foil, are spherically curved and that the outer lens (2) is provided with a hygroscopic coating (7) on its inner side.

* * * * *